US007169353B1

(12) United States Patent
Colin et al.

(10) Patent No.: US 7,169,353 B1
(45) Date of Patent: Jan. 30, 2007

(54) APPARATUS ENABLING LIQUID TRANSFER BY CAPILLARY ACTION THEREIN

(75) Inventors: Bruno Colin, Marcy I'Etoile (FR); Marie Privat, Saint Romain en Gal (FR)

(73) Assignee: Biomerieux S.A., Marcy l'Etoile (FR)

( * ) Notice: Subject to any disclaimer, the term of this patent is extended or adjusted under 35 U.S.C. 154(b) by 0 days.

(21) Appl. No.: 09/936,077

(22) PCT Filed: Mar. 9, 2000

(86) PCT No.: PCT/FR00/00581

§ 371 (c)(1), (2), (4) Date: Dec. 3, 2001

(87) PCT Pub. No.: WO00/53321

PCT Pub. Date: Sep. 14, 2000

(30) Foreign Application Priority Data

Mar. 9, 1999 (FR) .................................. 99 03034

(51) Int. Cl.
*G01N 33/00* (2006.01)

(52) U.S. Cl. ........................................ 422/57; 422/100

(58) Field of Classification Search ................ 422/102, 422/56–58, 100
See application file for complete search history.

(56) References Cited

U.S. PATENT DOCUMENTS 3,925,166 A 12/1975 Blume ........................ 195/139
4,260,687 A 4/1981 Jacobson et al. ........... 435/301
4,314,605 A * 2/1982 Sumitomo et al. .......... 165/110
4,318,994 A 3/1982 Meyer et al. ............... 435/301
4,676,274 A * 6/1987 Brown ........................ 137/806
4,756,884 A * 7/1988 Hillman et al. ............... 422/73
4,761,381 A 8/1988 Blatt et al. .................. 436/165
4,788,154 A 11/1988 Guigan ....................... 436/180
4,812,294 A 3/1989 Combs ........................ 422/72
5,230,866 A 7/1993 Shartle et al. .............. 422/103
5,242,606 A * 9/1993 Braynin et al. ............. 210/787
5,279,791 A * 1/1994 Aldrich et al. ................ 422/58
5,286,454 A * 2/1994 Nilsson et al. .............. 422/102
5,288,463 A 2/1994 Chemelli ..................... 422/58
5,413,872 A * 5/1995 Faigle ........................ 428/603

(Continued)

FOREIGN PATENT DOCUMENTS

EP 192794 9/1986

(Continued)

*Primary Examiner*—Jill Warden
(74) *Attorney, Agent, or Firm*—James C. Lydon

(57) ABSTRACT

An apparatus (1) which includes at least one planar surface (2) having compartments (3) which are defined by a partition (4), the compartments creating a space which makes it possible to displace at least one liquid sample (5 and/or 15) and, when there are at least two liquid samples (5 and 15), makes it possible to displace them both in an independent way and bring them together so that they can react with one another. The compartments (3) include at least two different types of groove: a deep groove (6), capable of partitioning the sample(s) (5 and/or 15), and a shallow groove capable of receiving the sample (s) (5 and/or 15), the two types of groove (6 and 16) making it possible to direct sample movements (5 and/or 15) by altering the orientation of the apparatus (1). The invention is particularly applicable for the micromanipulation of fluids in biological applications.

5 Claims, 3 Drawing Sheets

U.S. PATENT DOCUMENTS

| | | | | |
|---|---|---|---|---|
| 5,472,603 | A | 12/1995 | Schembri | 210/380.1 |
| 5,472,671 | A * | 12/1995 | Nilsson et al. | 422/102 |
| 5,595,712 | A | 1/1997 | Harbster et al. | 422/129 |
| 5,766,553 | A | 6/1998 | Staples et al. | 422/102 |
| 5,811,296 | A | 9/1998 | Chemelli et al. | 435/287.2 |
| 6,015,531 | A | 1/2000 | Colin et al. | 422/58 |
| 6,124,138 | A | 9/2000 | Woudenberg | 436/518 |
| 6,171,870 | B1 * | 1/2001 | Freitag | 436/518 |
| 6,582,662 | B1 * | 6/2003 | Kellogg et al. | 422/72 |

FOREIGN PATENT DOCUMENTS

| | | |
|---|---|---|
| EP | 282840 | 9/1988 |
| EP | 297 394 | 1/1989 |
| EP | 674009 | 9/1995 |
| EP | 705978 | 4/1996 |
| EP | 803288 | 10/1997 |
| WO | WO 94/26414 | 11/1994 |
| WO | WO 97/27324 | 7/1997 |
| WO | WO 97/36681 | 10/1997 |
| WO | WO 98/07069 | 2/1998 |
| WO | WO 98/55852 | 12/1998 |

* cited by examiner

Section A-A

APPARATUS ENABLING LIQUID TRANSFER BY CAPILLARY ACTION THEREIN

This application is a U.S. National Stage of International application PCT/FR00/00581, filed Mar. 9, 2000 and published on Sep. 14, 2000 in the French Language.

This invention concerns an apparatus wherein compartments are defined by a partition, thus creating a space in which at least one liquid sample can be displaced in a directed and independent fashion. When there are at least two liquid samples, they can both be displaced in an independent way and brought together so that they can react with one another.

Many documents in the background art deal with exploiting capillary action in fluid micromanipulation applications. Thus, document GB-A-2.261.284 pertains to an apparatus for transferring liquids for the purposes of diagnostic testing. This apparatus is based on channels made of a porous material.

In this embodiment, the capillary action of a porous material is used. This requires the incorporation of this porous material and it also necessitates having an impermeable separation between the two porous channels which both contain different liquids. In consequence, this method is fairly expensive to implement.

Patent U.S. Pat. No. 5,842,787 relates to fluid micromanipulation systems which include channels of varying dimensions. It is essentially the depth of the channels which can be modified although such variation also affects width so that the deeper the channel, the smaller its width (and vice versa). Unfortunately, these channels are not open; in other words, the liquids which are to be transferred inside the channels normally occupy the entire cross-sectional volume. As a result there are strong retention forces which inhibit the displacement of the liquids and therefore mean that sophisticated transfer systems are required (e.g. powerful pumps, the use of a vacuum, etc.).

In patent U.S. Pat. No. 5,660,993, capillary action is used to create a valve where two capillary channels meet. Apart from this novel function of opening up and shutting down liquid flow, exactly the same problems are encountered as with the previous document-because the channels are closed, retention is a problem.

According to documents EP-A-0.075.605 and WO-A-99/55852, shallow and deep grooves are combined to direct liquids. However, there is no description of the use of any physical property (neither capillarity nor any other physical phenomenon) in association with the deep and shallow grooves, and no such association is obvious to those skilled in the art.

In accordance with this invention, the apparatus proposed resolves all the problems mentioned in that it uses capillary action to move liquids while, at the same time, it minimizes retention phenomena. This makes for perfectly effective directed displacement, even in the presence of a free space which means that the transferred liquid is not physically confined.

To this effect, this invention concerns an apparatus comprising at least one planar surface whereat compartments are found and are defined by a partition, the compartments creating a space which makes it possible to displace at least one liquid sample in an independent fashion and, when there are at least two liquid samples, makes it possible to displace them both independently and bring them together to react with one another, characterized in that the compartments consist of at least two different types of groove:

a first type of groove, said to be deep, serving as a partitioning means of the sample(s), the depth of the deep groove(s) in relation to the partition being such that capillary action is not enabled, and a second type of groove, said to be shallow, serving as a receiving means for said sample(s), the depth of the shallow groove(s) in relation to the partition being such that capillary action is enabled, the two types of groove making it possible to direct sample movements by altering the orientation of the device.

According to a preferred embodiment variation, the width of each deep groove is such that that capillary action is not enabled. According to another embodiment variation or another embodiment, there is at least one shallow groove adjacent to a deep groove.

According to another embodiment, which might be complementary to the preceding one, there is at least one deep groove adjacent to a shallow groove.

Preferably, whatever the embodiment, one deep groove is located between two shallow grooves. In this case, the deep groove has an end where the two shallow grooves meet to create a reaction zone.

According to a first embodiment, the distance between the reaction zone and the partition or the partitioning film is such that capillary action is enabled.

According to a second embodiment, the distance between the reaction zone and the partition or the partitioning film is such that capillary action is not enabled.

The Figures herewith are given by way of example and are not to be taken as in any way limiting. They are intended to make the invention easier to understand.

Figure 1:
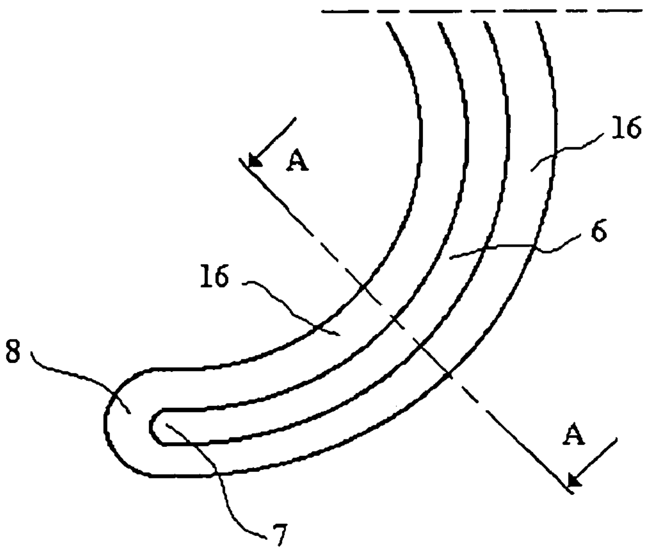
FIG. 1 shows an overhead view of the side of the apparatus with the compartment according to the invention.
Figure 2:
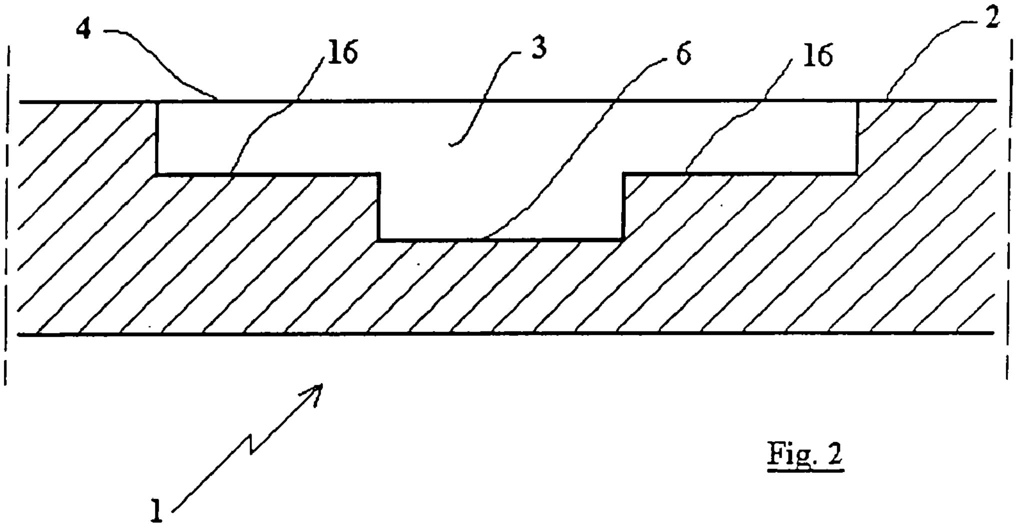
FIG. 2 shows a partial, transverse cross-section through A—A in FIG. 1.
Figure 6:
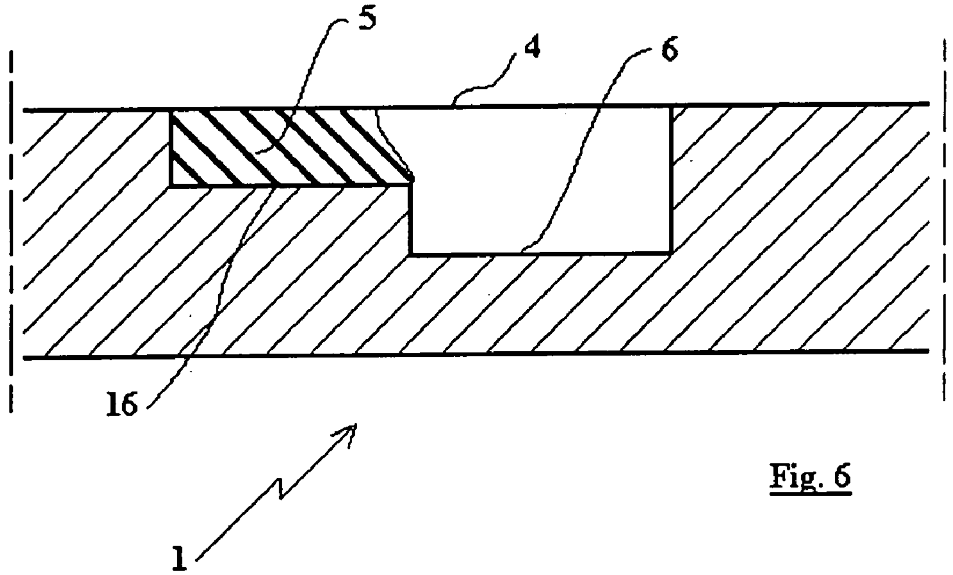

Finally, FIG. 6 shows a cross-section exactly like that in FIG. 2, but of a third embodiment of this invention containing a liquid sample.

This invention relates to an apparatus (1) which is clearly illustrated in FIGS. 2 through 6 which are partial, transverse cross-sections through three different embodiments. Such an apparatus (1) can be used for the analysis of one or more different liquid samples to identify one or more analytes, using any method, be it a simple or complex method and be it based on one or more different reagents, depending on the chemical, physical or biological nature of the analyte being tested. The technical principles defined hereafter are not restricted to any single, specific analyte; the only required condition is that the analyte must either be dissolved or in suspension in the test sample. In particular, the test process being used can be performed on a homogenous, heterogeneous or mixed form.

One particular, non limited mode of such a device, concerns biological tests for the detection and/or quantitative determination of one or more ligands, in which the assay involves one or more anti-ligands. The word ligand is taken to mean any biological species, e.g. an antigen, a fragment of an antigen, a hapten, a nucleic acid, a fragment of nucleic acid, a hormone or a vitamin. One example of an application of the test methods concerns immunoassays, whatever their particulars and whether the assay is direct or based on competition. Another example of an application concerns the detection and/or quantitative determination of nucleic acids, including all operations required for such detection and/or quantitation in any kind of sample containing the target nucleic acid species. Among such diverse operations, the following could be specified: lysis, melting, concentration, enzyme-mediated nucleic acid amplification, and any detection modalities which include a hybridization step using, for example, a DNA chip or a labeled probe. Patent application WO-A-97/02357 stipulates the various stages involved in the case of nucleic acid analysis.

In a particularly interesting embodiment shown in FIGS. 1 to 4, it can be seen that the apparatus (1) actually consists of a card with two sides, an upper and a lower side which are parallel to one another. Of course, it does not necessarily have to be used in a horizontal position-it can also be used in a vertical position or on a slope.

In the Figures, both sides are planar but it is the upper side which is of greater interest for this invention. Thus, the upper planar surface (2) of the apparatus (1) includes cavities which create the compartments (3). The compartments are partitioned off with respect to the surfaces that are flush with the surface (2) by means of a film or partition (4). This compartment (3) thus isolated actually consists of a set of different forms. On the sides, there are two shallow grooves (16) and in the middle there is one deep groove (6). The view in FIG. 2 corresponds to a partial cross-section through A—A in FIG. 1. From FIG. 1, it can be seen that the two shallow grooves (16) are parallel to one another for the entire length of the deep groove (6). However, one of the ends of the deep groove (6) has an end (7) and the two shallow grooves (16) meet there to create a reaction zone (8).

Figure 3:
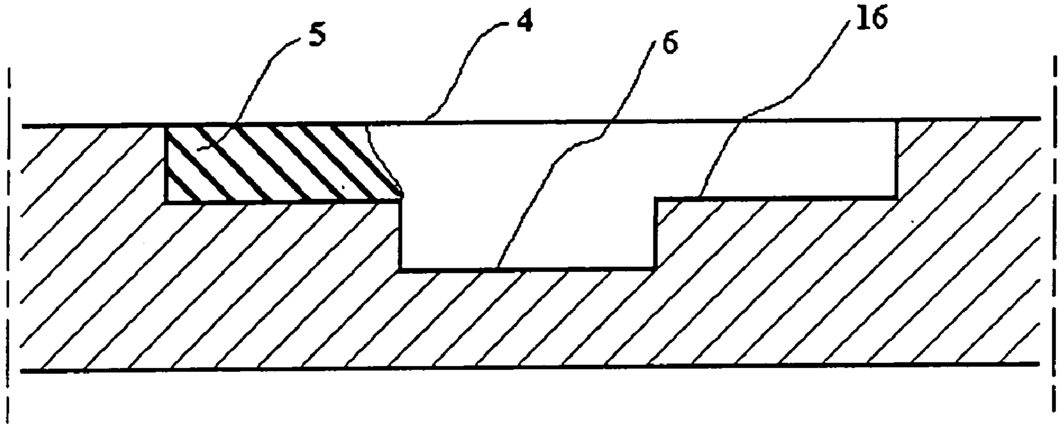
FIG. 3 shows exactly the same view as FIG. 2 but with a liquid sample present.
Figure 4:
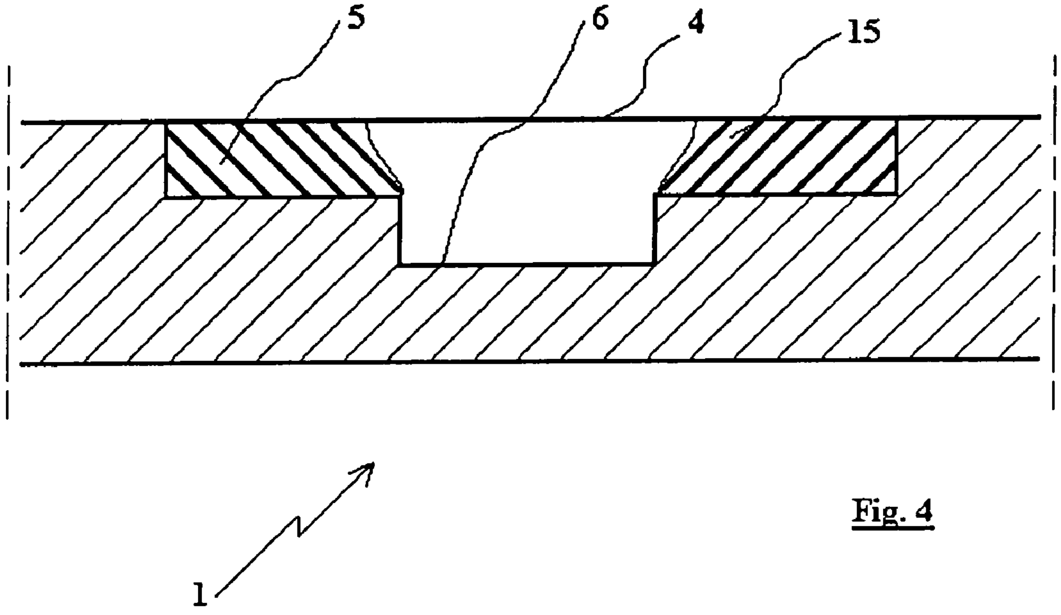
FIG. 4 shows exactly the same view as FIGS. 2 and 3 but with two different liquid samples present.

It is possible to isolate a first liquid sample (5) in one of the shallow grooves (16), as shown in FIG. 3. Similarly, it is possible to isolate another liquid sample (15) in the other shallow groove (16), as shown in FIG. 4. In practice, to insure that liquids (5) and (15) remain in position in the shallow grooves (16) without mixing, the distance separating the bottom of the groove (16) and the partitioning film (4) should be small enough for capillary action to take place. The ideal distance between the film (4) and the bottom of the groove (16) for capillary action is between 50 and 800 micrometers (μm) (preferably between 300 and 500 μm). In the case of an apparatus consisting of a card made of impact polystyrene and a BOPP film being used to transfer an aqueous solution containing 9 g/liter NaCl, 1 g/liter $NaN_3$ and 1 ml/l of either Tween 20 (registered trademark) or Triton X100 (registered trademark), the distance between the film (4) and the bottom of the groove (16) might be set at 400 μm. This dimension is actually typical for the kinds of liquid (5 and/or 15) which are likely to be used in this apparatus (1), given the materials used to make the apparatus (1). This distance may have to be varied for various reasons, e.g. depending on the viscosity, density, wetting activity and surface tension of the liquids being used, and on the hydrophilic/hydrophobic properties of the materials used to make the film and the card.

In contrast, the distance separating the film (4) from the bottom of the deep groove (6) must be great enough to insure that capillary action does not lead to the retention of liquid (5 or 15) here. Of course, it is obvious that the width value of this deep groove must be such that capillary action cannot take place.

The nature of the flexible film may vary according to the nature of the test card and of the fluids being tested, especially when compatibility is at issue. For example, TPX (polymethyl pentene copolymer) or BOPP (bi-oriented polypropylene) films are suitable for biological assays. These films can be fixed in place either using an adhesive (with the adhesive applied to the film, e.g. a silicon-based adhesive) or by heat-sealing. An example of a BOPP adhesive is available from BioMérieux Inc. (St. Louis, Mo., USA) (reference: 022004-2184).

In terms of production, the test cards are manufactured by the machining of special plastic material, e.g. impact polystyrene (reference: R540E from the Goodfellow company) which is compatible with the liquids being processed. For industrial-scale production, the card could be manufactured by precision molding, but any other manufacturing method (including those used in the semi-conductor industry as stipulated in patent application WO-A-97/02357) may be used for test card production.

Figure 5:
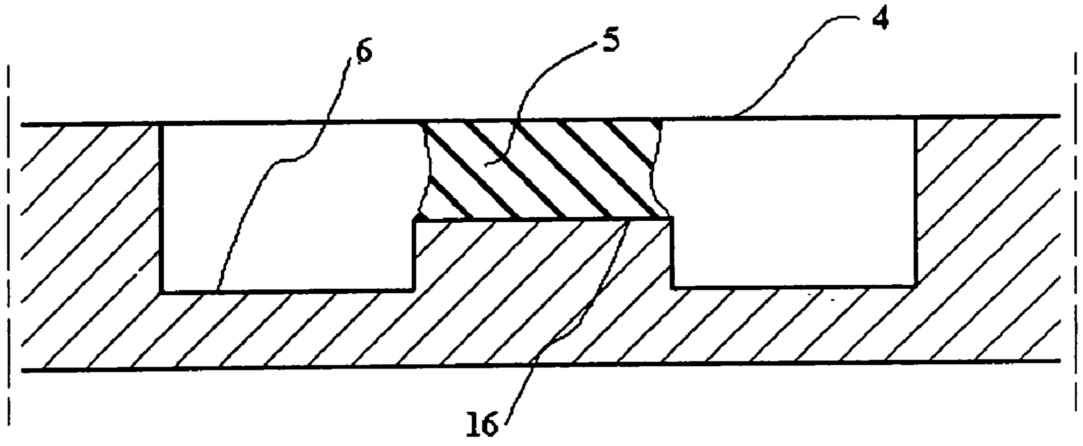
FIG. 5 shows a cross-section exactly like that in FIG. 2, but of a second embodiment containing a liquid sample.

Of course, a number of other embodiments can be imagined and two of these are shown in FIGS. 5 and 6. That in FIG. 5 corresponds to a substantially reversed configuration of the first embodiment shown in FIGS. 1 to 4. Thus, in FIG. 5, one shallow groove (16) occupies the central position between two deep grooves (6). The liquid sample (5) is only in contact with the bottom of the shallow groove (16).

In another embodiment shown in FIG. 6, it is possible to have a single shallow groove (16) and a single deep groove (6).

Of course, all permutations are possible and can be imagined. For example, there might be a whole series of deep grooves (6) or shallow grooves (16). The only prerequisite condition is that the deep grooves (6) be located between the shallow grooves, (16) or vice versa. Liquids (5 and/or 15) can be introduced by means of valves, pumps, and/or channels, as described in the patent applications submitted by the applicant on the same day with the following titles:

"A device and a method for positioning a liquid", for the first document,

"A pumping device for transferring at least one fluid into a consumable," for the second document, and finally "A test sample card with improved filling" for the third document.

The liquids (5 and 15) can be moved in different ways, e.g. the card (1) could be made to vibrate or it could be placed in a substantially vertical position so that the liquids are driven by the force of gravity; alternatively, centrifugal force could be used. Pumping systems could be used, either located inside or outside the card; these could be based on diaphragm pumps (U.S. Pat. No. 5,277,556), piezoelectric peristaltic pumps (U.S. Pat. No. 5,126,022), ferrofluid transport systems, or electric and hydrodynamic pumps (Richter et al., Sensors and Actuators, 29, p159–165, 1991). Combinations of more than one of these types of system could also be used.

REFERENCES

1. Apparatus
2. Planar surface of the apparatus (1)
3. Compartments
4. Partition or partitioning film
5. First liquid sample
6. First type of groove, said to be deep
7. End of the groove (6)
8. Reaction zone
15. Second liquid sample
16. Second type of groove, said to be shallow

The invention claimed is:

1. A test card comprising at least one planar surface wherein at least two compartments are made and defined by a partition comprising a film, the compartments creating a space which makes it possible to displace at least two liquid samples independently of one another, the compartments comprising at least two different types of grooves:

at least one deep groove capable of partitioning samples from one another, the depth and the width of the deep groove in relation to the partition being such that capillary action of a sample is not enabled, and at least two shallow grooves, each of the shallow grooves being capable of receiving one of the samples, respectively, the depth of shallow grooves in relation to the partition being such that capillary action of the sample is enabled, each shallow groove being adjacent to the deep groove, along the entire length of said deep groove, wherein said test card is adapted for analysis of chemical, biochemical or biological analytes.

2. The test card of claim 1, wherein a deep groove is positioned between two shallow grooves.

3. The test card of claim 2, wherein the two shallow grooves meet at one of the ends of the deep groove to create a reaction zone there, where the two liquid samples may be brought together.

4. The test card of claim 3, wherein the distance between the reaction zone and the partition is such that capillary action is enabled.

5. The test card of claim 3, wherein the distance between the reaction zone and the partition is such that capillary action is not enabled.

* * * * *